United States Patent [19]

Haviv et al.

[11] Patent Number: 5,432,263
[45] Date of Patent: Jul. 11, 1995

[54] PROCESS FOR PRODUCING PEPTIDES WITH SIDE CHAINS CONTAINING IMIDAZOLINYLAMINO, TETRAHYDROPYRIMIDINYLAMINO, OR ALKYLGUANIDINYL GROUPS

[75] Inventors: Fortuna Haviv, Deerfield; Rolf E. Swenson, Grayslake, both of Ill.; Timothy D. Fitzpatrick, Boulder, Colo.

[73] Assignee: Abbott Laboratories, Abbott Park, Ill.

[21] Appl. No.: 188,293

[22] Filed: Jan. 28, 1994

Related U.S. Application Data

[63] Continuation-in-part of Ser. No. 993,200, Dec. 18, 1992, abandoned.

[51] Int. Cl.$^6$ ............................................. A61K 38/00
[52] U.S. Cl. ................................. 530/345; 530/333; 530/337; 530/336
[58] Field of Search ................ 530/333, 334, 337, 345

[56] References Cited

PUBLICATIONS

Theobald, J Am Chem Soc 112, 9624 (1990).
J. Med. Chem., Nesto, Jr., et al., "Potent Gonadotropin Releasing Hormone Antagonists with Low Histamine-Releasing Activity", pp. 3942–3948, vol. 35, published 1992.

*Primary Examiner*—Jill Warden
*Assistant Examiner*—David Lukton
*Attorney, Agent, or Firm*—Jerry F. Janssen

[57] ABSTRACT

The present invention provides a process for the preparation of peptides which have or side-chains containing an alkyl- or dialkyl-substituted guanidinyl group or a imidazinylamino or tetrahydropyrimidinylamino group. The process provides higher overall yields of peptide product by permitting the synthesis of the entire peptide chain prior to modification of the side-chain to introduce the groups.

6 Claims, No Drawings

PROCESS FOR PRODUCING PEPTIDES WITH SIDE CHAINS CONTAINING IMIDAZOLINYLAMINO, TETRAHYDROPYRIMIDINYLAMINO, OR ALKYLGUANIDINYL GROUPS

CROSS REFERENCE TO RELATED APPLICATIONS

This application is a continuation-in-part of application Ser. No. 07/993,200 filed Dec. 18, 1992, now abandoned.

TECHNICAL FIELD

The present invention relates to chemical processes for producing peptides. More particularly this invention concerns an improved process for introducing side-chains containing an alkyl- or dialkylguanidinyl group or an imidazolinylamino or tetrahydropyrimidinylamino group into peptides.

BACKGROUND OF THE INVENTION

Peptides having alkyl- and dialkylguanidinyl-containing side chains or imidazolinylamino- or tetrahydropyrimidinylamino-containing side chains are frequently useful as pharmaceutical agents. Typically these peptides have been produced by first synthesizing the individual amino acids containing the desired side-chain modification, protecting the reactive side-chain groups in the various amino acids, and subsequently linking the individual modified amino acids to a resin form a peptide using conventional methods. This conventional method is the solid phase method set forth in Merrifield, R. B. *J. Am Chem. Soc.* 1963, 85, 2149. This process of first synthesizing the protected amino acids containing the desired side chain modification and then synthesizing the peptide is typically a difficult and expensive one, often yielding relatively small amounts of the desired peptide. There is thus a need in the an for a process whereby peptides containing imidazolinylamino- or tetrahydropyrimidinylamino-containing side chains or alkylguanidinyl or dialkylguanidinyl-containing side chains can be more readily introduced into peptides using solid phase peptide synthesis techniques.

SUMMARY OF THE INVENTION

In accordance with the present invention there is provided a process for readily introducing one or more side-chains containing an alkyl- or dialkyl-guanidinyl group or an imidazolinylamino or tetrahydropyrimidinylamino group into an existing peptide or peptide fragment. The process of this invention provides efficiencies of synthesis and higher overall yields of the peptide end-products by permitting the synthesis of the entire peptide chain or, alternatively, large segments of the final peptide prior to the side-chain modification..

The present invention provides for a method of preparing peptides containing one or more aminoacyl residues of the structure

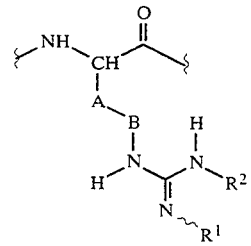

wherein A and B are selected from the group consisting of divalent straight or branched alkylene of from 1 to 8 carbon atoms and cis- or trans- 1,4-cyclohexylene, with the proviso that A and B may not both be cyclohexylene. $R^1$ and $R^2$ are independently selected from the group consisting of hydrogen, straight or branched alkyl of 1 to 6 carbon atoms, $-(CH_2)_mO(CH_2)_nCH_3$ wherein m is an integer of 2 to 4, inclusive, and n is an integer of 1 to 4, inclusive, with the proviso that $R^1$ and $R^2$ may not both be hydrogen. Alternatively, $R^1$ and $R^2$ are joined, together with the nitrogen atoms to which they are attached to form a 5- or 6-membered ring. In the structure shown above, the unsatisfied valence bonds are understood to be the sites of attachment of the designated aminoacyl residue to the remainder of the peptide chain.

The process of this invention comprises the steps of first (a) reacting the free amino group in the side chain of the aminoacyl residue of a functionally-protected resin-bound peptide containing an amino acyl residue of the structure

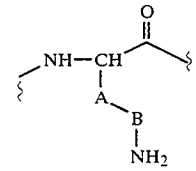

with 1,1'-thiocarbonyldiimidazole to form the imidazolylthiocarbonyl compound of the structure

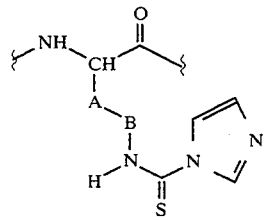

where A and B are defined as above.

In the next step, (b), the product of step (a) is treated with an amine, $R^3NH_2$, where $R^3$ is selected from the group consisting of hydrogen, straight or branched alkyl of 1 to 6 carbon atoms, $-(CH_2)_mO(CH_2)_nCH_3$, where m and n are defined above, and 1,2-diaminoethane, and 1,3-diaminopropane in which one of the amino groups is protected, to form a thiourea of the formula

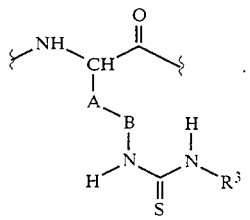

In the next step, (c), the product of step (b) is treated with methyl iodide to form the isothiuronium iodide intermediate of the formula

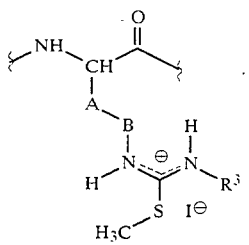

In the final step, (d), the isothiuronium iodide product of step (c), when $R^3$ is hydrogen or straight or branched alkyl of 1 to 6 carbon atoms or —$(CH_2)_mO(CH_2)_nCH_3$, the isothiuronium iodide intermediate product of step (c) is reacted with an amine $R^4NH_2$ where $R^4$ is selected from the group consisting of hydrogen, straight or branched alkyl of 1 to 6 carbon atoms and —$(CH_2)_mO(CH_2)_nCH_3$, provided that $R^3$ and $R^4$ are not both hydrogen, to form a product of the structure

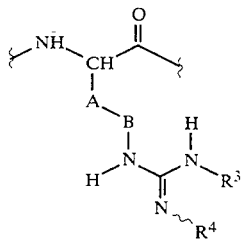

and, alternatively, when $R^3$ in the isothiuronium iodide product of step (c) is protected 2-aminoethyl or protected 3-aminopropyl, is deprotected and then allowed to react intramolecularly in the presence of a base to form a product of the formula

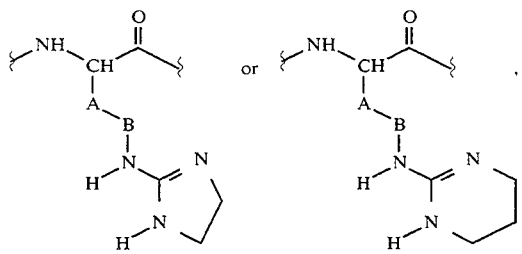

respectively.

DETAILED DESCRIPTION AND PREFERRED EMBODIMENTS

As used throughout this specification and the mended claims, the term "halide" as used herein refers to bromo (Br), chloro (Cl), fluoro (F) or iodo (I).

The terms "resin" or "peptide resin" as used herein refer to neutral resins of the type commonly used in the an of synthetic peptide preparation. Examples of such resins include, but are not limited to, 4-methylbenzhydrylamine (MBHA) or benzhydrylamine (BHA) or Merrifield resin.

The term "alkyl" as used herein refers to a monovalent radical derived from a straight or branched saturated hydrocarbon by the removal of a single hydrogen atom. Examples of alkyl include, but are not limited to methyl, ethyl, propyl, isopropyl, butyl, sec-butyl, isobutyl, tert-butyl, pentyl, hexyl, and the like.

The term "alkylene" refers to a straight or branched divalent group derived from a saturated hydrocarbon by the removal of two hydrogen atoms. Examples of alkylene include —$CH_2$—, —$CH_2CH_2$—, —$CH(CH_3)CH_2$— and the like.

The term "cycloalkyl" refers to a monovalent cyclic hydrocarbon group derived from a cyclic saturated hydrocarbon group by the removal of a single hydrogen atom. Examples of cycloalkyl groups include cyclopropyl, cyclobutyl, cyclohexyl, cycloheptyl, bicyclo[2.2.2]octane, and the like.

The term "cycloalkylene" refers to a divalent group derived from a saturated cyclic hydrocarbon by the removal to two hydrogens. Examples include cyclopentylene, cycohexylene, and the like. For the most part, the names of natrurally-occuring and non-naturally-occuring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)," *Biochemistry, 14 (2)*: 1975), which is incorporated herein by reference. To the extent that the names and abbreviations employed in this specification and appended claims differ from those suggestions, they will be made clear to the reader by the following table.

| Abbreviation | Amino Acyl Residue Abbreviations |
|---|---|
| | Definition |
| | Alanyl & Derivatives |
| Ala | L-Alanyl |
| D-Ala | D-Alanyl |
| L-AlaNH2 | L-Alanylamide |
| D-AlaNH2 | D-Alanylamide |
| D-1-Nal | D-3-(Naphth-1-yl)alanyl |
| D-2-Nal | D-3-(Naphth-2-yl)alanyl |
| N-Ac-1-Nal | N-Acetyl-L-3-(Naphth-1-yl)alanyl |
| N-Ac-2-Nal | N-Acetyl-L-3-(Naphth-2-yl)alanyl |
| N-Ac-D-1-Nal | N-Acetyl-D-3-(Naphth-1-yl)alanyl |
| N-Ac-D-2-Nal | N-Acetyl-D-3-(Naphth-2-yl)alanyl |
| 2-Pal | L-3-(Pyrid-2-yl)alanyl |
| 3-Pal | L-3-(Pyrid-3-yl)alanyl |
| 4-Pal | L-3-(Pyrid-4-yl)alanyl |
| D-2-Pal | D-3-(Pyrid-2-yl)alanyl |
| D-3-Pal | D-3-(Pyrid-3-yl)alanyl |
| D-4-Pal | D-3-(Pyrid-4-yl)alanyl |
| | Arginyl & Derivatives |
| Arg | L-Arginyl |
| D-Arg | D-Arginyl |
| Harg | L-Homoarginyl |
| | (I.e. L-2-Amino-6-guanidinohexanoyl) |
| D-Harg | D-Homoarginyl |

-continued

| Amino Acyl Residue Abbreviations | |
|---|---|
| Abbreviation | Definition |
| Harg(Et) | L-2-Amino-6-$N^G$-ethylguanidino-hexanoyl) (I.e. D-2-Amino-6-guanidinohexanoyl) |
| Harg(Et)$_2$ or Harg(Diethyl) | L-2-Amino-6-$N^G$,$N^G$-diethylguanidino-hexanoyl) |
| N-MeHarg | N-Methyl-L-homoarginyl |
| Harg(CH$_2$)$_2$ | L-2-Amino-5-(amino-6-(aminoimidazol-2-yl)hex-anoyl |
| *Glycyl & Derivatives* | |
| Gly | Glycyl |
| N-Ac-Gly | N-Acetylglycyl |
| *Leucyl, Isoleucyl & Derivatives* | |
| Ile | L-Isoleucyl |
| D-Ile | D-Isoleucyl |
| Leu | L-Leucyl |
| D-Leu | D-Leucyl |
| *Lysyl & Derivatives* | |
| Lys | L-Lysyl |
| D-Lys | D-Lysyl |
| Lys(Nic) | L-(N'-epsilon-Nicotinyl)lysyl |
| D-Lys(Nic) | D-(N'-epsilon-Nicotinyl)lysyl |
| *Ornithyl & Derivatives* | |
| Orn | Ornithyl (I.e. α,δ-Diaminovaleryl) |
| D-Orn | D-Ornithyl |
| Cit | Citrullyl (I.e. N'-delta-Aminocarbonyl-L-ornithyl) |
| D-Cit | D-Citrullyl |
| Hcit | Homocitrullyl (I.e. L-2-Amino-(6-aminocarbonylamino)-hexanoyl |
| D-HCit | D-Homocitrullyl |
| *Phenylalanyl & Derivatives* | |
| Phe | L-Phenylalanyl |
| D-Phe | D-Phenylalanyl |
| 4-Cl-Phe | L-3-(4-Chlorophenyl)alanyl |
| D-4-Cl-Phe | D-3-(4-Chlorophenyl)alanyl |
| 2,4-Cl-Phe | L-3-(2,4-Dichlorophenyl)alanyl) |
| 4-F-Phe | L,3-(4-Fluorophenyl)alanyl |
| D-4-F-Phe | D-3-(4-Fluorophenyl)alanyl |
| N-Ac-Phe | N-Acetyl-L-phenylalanyl |
| N-Ac-D-Phe | N-Acetyl-D-phenylalanyl |
| *Prolyl & Derivatives* | |
| Pro | L-Prolyl |
| D-Pro | D-Prolyl |
| Pro(OH) | L-4-Hydroxyproline |
| D-Pro(OH) | D-4-Hydroxyproline |
| DePro or $\Delta^{3,4}$-Pro | 3,4-Didehydro-L-prolyl |
| *Seryl & Derivatives* | |
| Ser | L-Seryl |
| D-Ser | D-Seryl |
| Hser | L-Homoseryl |
| *Tryptophyl & Derivatives* | |
| Trp | L-Tryptyl |
| D-Trp | D-Tryptyl |
| Trp(Me) | L-(N-indole-methyl)Tryptyl |
| *Tyrosyl & Derivatives* | |
| Tyr | L-Tyrosyl |
| D-Tyr | D-Tyrosyl |
| N-Me-Tyr | N-α-Methyl-L-tyrosyl |
| N-Me-D-Tyr | N-α-Methyl-D-tyrosyl |
| Tyr(OBz) | O-Benzyl-L-tyrosyl |
| Tyr(OMe) | O-Methyl-L-tyrosyl |
| D-Tyr(OBz) | O-Benzyl-D-tyrosyl |
| D-Try(OMe) | O-Methyl-D-tyrosyl |

The method of the present invention is particularly useful for the synthesis of peptides of from two to twenty aminoacyl residues which contain one or two aminoacyl residues which have the side-chain modification resulting from the process of the present invention. However, the process can be used to prepare larger peptides having more than one side-chain modification of the type contemplated in this invention by the simple expedient of preparing oligopeptide segments, each having the desired side-chain modifications, and then linking the oligopeptide segments in the conventional manner to form the larger final peptide product.

In those cases where the desired product of the reaction is a peptide containing a single side-chain modification of the type contemplated by this invention, the reaction sequence described above is carried out after first protecting other side-chain functional groups in the peptide with protecting groups known in the art. A detailed description of such protecting groups is found, for example, in M. Bodanszky and A. Badanszky, "The Practice of Peptide Synthesis," Springer-Verlag, New York, 1984, pp. 151–195 and in M. Bodanszky and A. Badanszky, "Principles of Peptide Synthesis," Springer-Verlag, New York, 1984, pp. 202–226.

In the case where the desired product is a peptide containing two aminoacyl residues having the side-chain modification of the process of this invention, the peptide is constructed of amino acid residues in which which reactive side-chain groups are fast protected. The side-chain amino functions of the two amino acid residues in question are "orthoganally" protected. That is, the side chain amino group of one amino acid residue is protected with an "Fmoc" (fluorenylmethoxycarbonyl) protecting group and the other with a Cbz (benzyloxycarbonyl) protecting group. Following coupling of the protected amino acid residue to form the peptide, the protecting group on one amino side chain is removed by conventional methods without deprotecting the other protected amino side chain. The unprotected side chain amino group is then modified by the process of the present invention. Subsequent deprotection of the other protected amino side chain group and processing with the method of this invention can produce a modified side chain of the same or different structure from the first. In a similar manner, the second amino side chain, once deprotected, can be allowed to remain a simple amino side chain functional group. In this manner it is possible, for example, to produce peptides in which a lysyl amino acid residue is left unchanged by the process while an amino-containing side chain at another site in the peptide is modified.

In the case of the synthesis of a peptide where the side chain amino groups have to be modified, it is also possible to sequentially couple the protected amino acid residues using peptide solid phase synthesis techniques to build the peptide up to the point where the first modification is to be made. An aminoacyl residue having an N-alpha-BOC protecting group and an FMOC side-chain protecting group is coupled to the growing peptide chain. The side chain amino group is then deprotected by treatment with a secondary amine and modified as desired by the process of the present invention. The N-alpha BOC protecting group is then cleaved by treatment with TFA and the synthesis of the peptide chain is continued Additional side chain modifications further along the growing peptide chain are made by repeating this series of steps.

If the desired peptide end-product is one in which two amino acid residues possessing amino side chain groups are to be similarly modified, the peptide is constructed of amino acid residues in which the amino function in the side chains of both residues are similarly protected before linking to form the peptide. Once linked, the protecting groups on both residues are both removed at the same time under the same conventional reaction conditions, and the process of the present invention is used to simultaneously modify both side chain sites.

When the desired peptide end-product contains three or more amino-functionalized side chains which are to be modified by the process of the present invention, the final peptide is constructed by linking di-, tri-, tetra-penta-, etc. or oligopeptide segments containing one or two modified sites which segments are prepared first by the method detailed above.

The polypeptides to which the side-chain modification process of the present invention may be applied are generally synthesized by techniques known to those skilled in the art as, for example, by so-called "solid phase" peptide synthesis or by usual methods of solution phase chemistry. A summary of available solid phase peptide synthetic techniques may be found in J. M. Stewart and J. D. Young, *Solid Phase Peptide Synthesis*, W. H. Freeman Co., San Francisco, 1963 and J. Meienhofer, *Hormonal Proteins and Peptides*, Vol. 2., p.46, Academic Press (New York), 1973. For classical solution synthesis see G. Schroder and K. Lupke, *The Peptides*, vol. 1, Academic Pres (New York), 1965.

In general, these methods comprise the sequential addition of one or more amino acids or suitably protected amino acids to a growing peptide. The starting amino acids are commercially available or, where novel in the compounds of this invention, are synthesized by methods detailed below from readily available starting materials.

Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conducive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing peptides involves solid phase peptide synthesis. In this method of preparing peptides, the alpha-amino function of the amino acids is protected by an acid sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (t-BOC), benzyloxycarbonyl (Cbz), biphenylisopropyloxycarbonyl, t-amyloxycarbonyl, isobornyloxycarbonyl, (alpha,alpha)-dimethyl-3,5dimethoxybenzyloxycarbonyl, o-nitrophenylsulfenyl, 2-cyano-t-butyloxycarbonyl, 9-fluorenylmethoxycarbonyl, (FMOC) and the like. The tert-butyloxycarbonyl ("BOC" or "t-BOC") protecting group is preferred.

Particularly preferred side chain protecting groups are, for side-chain amino groups in arginine: nitro, p-toluenesulfonyl, 4-methoxy-benzenesulfonyl, Cbz; for lysine: 9-fluorenylmethoxycarbonyl (FMOC), or CBZ; for tyrosine: benzyl, o-bromo-benzyloxycarbonyl, 2,6-dichlorobenzyl, isopropyl, cyclohexyl, cyclopentyl and acetyl; for serine: benzyl and tetrahydropyranyl; for histidine: benzyl, Cbz, p-toluenesulfonyl and 2,4-dinitrophenyl; for tryptophan: formyl; and for glutamyl or aspartyl: benzyl esters.

In the solid phase peptide synthesis method, the C-terminal amino acid is first attached to a suitable solid support. Suitable solid supports useful for the above synthesis are those materials which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. Chloromethyl-polystyrene-1% divinylbenzene polymer is especially preferred. For the special case where the C-terminus of the compound is glycinamide, a particularly useful support is the benzhydrylamino-polystyrene-divinylbenzene polymer described by P. Rivaille, et al, *Helv. Chim. Acta.*, 54, 2772 (1971). The coupling to the chloromethyl polystyrene-divinylbenzene type of resin is made by means of the reaction of the alpha-N-protected amino acid, especially the BOC-amino acid, as its cesium, tetramethylammonium, triethylammonium, 1,5-diazabicyclo-[5.4.0]undec-5-ene, or similar salt. The coupling reaction is accomplished in a solvent such as ethanol, acetonitrile, N,N-dimethylformamide (DMF), and the like, with the chloromethyl resin at an elevated temperature, for example between about 40° and 60° C., for from about 12 to 48 hours. Preferred reagents and reaction conditions involve the coupling of an alpha-N-BOC amino acid cesium salt with the resin in DMF at about 50° C. for about 24 hours. The alpha-N-BOC-amino acid is attached to the benzhydrylamine resin by means of N,N'-dicyclohexylcarbodiimide (DCC) or N,N'-diisopropylcarbodiimide (DIC) with or without 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), mediated coupling for from about 1 to about 24 hours, preferably about 12 hours at a temperature of between about 10° and 50° C., most preferably 25° C. in a solvent such as dichloromethane or DMF, preferably dichloromethane. The coupling of the carboxyl group to the N-methyl-Ser(OBzl) attached to the peptide resin requires catalysis by 4-dimethylaminopyridine (DMAP), in addition to the carbodiimide reagent.

The coupling of successive protected amino acids can be carded out in an automatic polypeptide synthesizer as is well known in the art. The removal of the BOC alpha-N-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in 0.4M concentration and approximately 3.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-isopropylcarbodiimide (DIC) or other carbodiimide either alone or in the presence of HOBt, N-hydroxysuccinimide, other N-hydroxyimides or oximes. Alternately, protected amino acid active ester (e.g. p-nitrophenyl, pentafluorophenyl and the like) or symmetrical anhydrides may be used.

Once the desired peptide has been prepared by one of the methods detailed above, the process of the present invention may be carried out for side-chain modification of the peptide. In this process the peptide, having at least one amino-group-bearing side chain, is subjected to the further process steps detailed in the following reaction scheme.

as piperidine or diethylamine to produce a peptide having an aminoacyl residue designated 1 above. The peptide is then treated for a period of one to three hours, preferably about one hour, with a solution made up of ten equivalents of 1'-thiocarbonyl-diimidazole in dimethylformamide. The 1,1'-thiocarbonyldiimidazole solution is then drained from the peptide-resin (resin) and the resin is washed several times, first with a ( 1: 1 ) solution of dichloromethane-dimethylformamide (DCM-DMF) and then DCM to form the aminothiocarbonylimidazolyl residue of formula 2.

In the next step of the process the peptide containing the amino acyl residue of formula 2 is treated for a

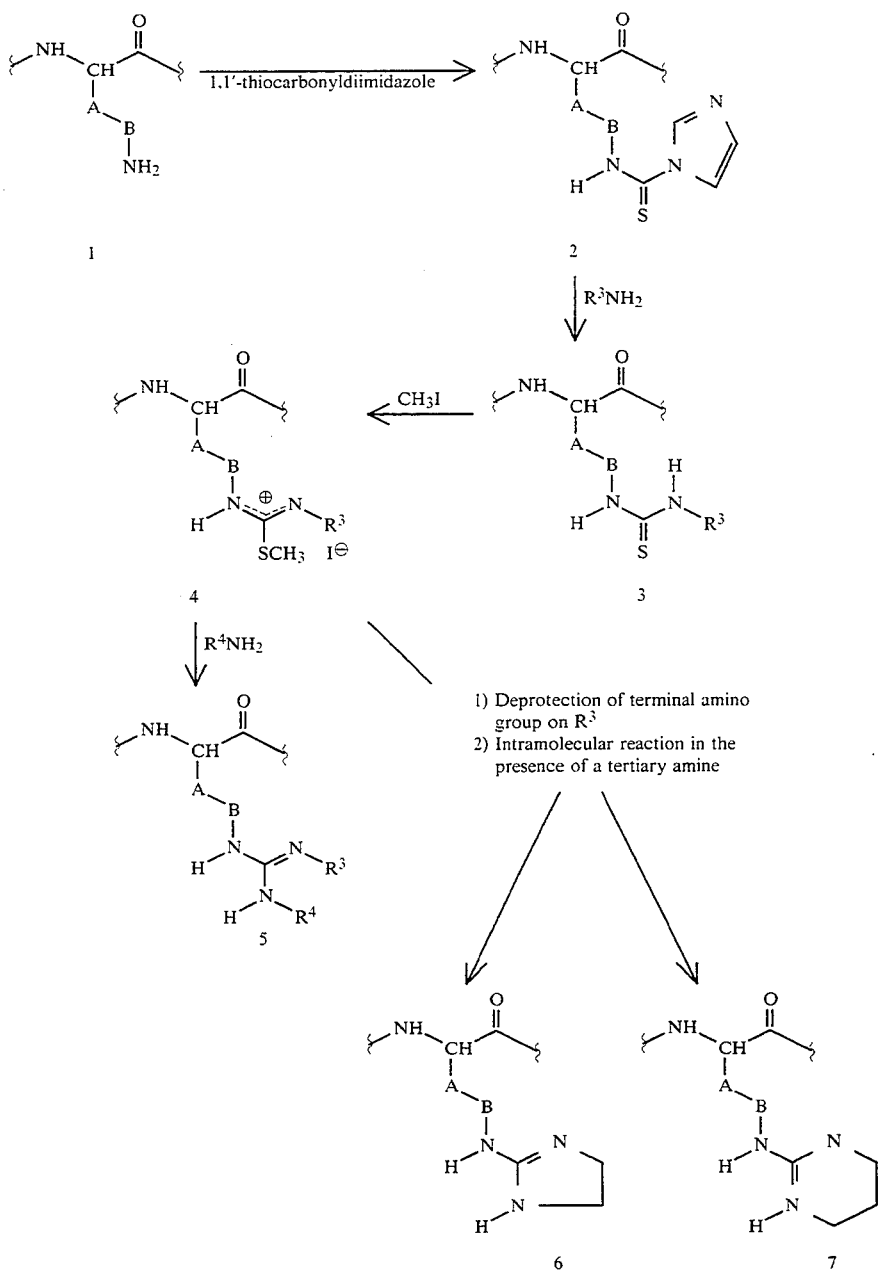

In this process, the peptide, preferably still attached to a peptide-resin (for example MBHA or BHA) and containing an amino acyl residue, having an amino group in the side chain blocked with FMOC, is first deprotected by treatment with a secondary amine such period of two to six hours, preferably about four hours, with a 10% solution of alkylamine or monoprotected diaminoalkane, $R^3NH_2$, in DMF. The alkyl amine (or monoprotected diaminoalkane) solution is then drained, and the same reaction is repeated for an additional period of eight to twelve hours. Upon completion of this reaction, the resin is washed with DCM/DMF and then DCM as above. The washed resin is then allowed to dry affording the amino acyl residue of formula 3.

At this point the peptide containing amino acyl residue 3 may be cleaved from the resin and further transformed in solution or further processing steps may be carried out with the peptide still attached to the resin. It has been found that when there are two or more amino-group-containing side chain groups on the peptide being modified by the process of this invention, the further steps are more efficiently carried out if the peptide is cleaved from the resin. While not holding to one theory to the exclusion of others, it is believed that this is due to the steric hindrance of the reactions caused when the peptide remains bound to the resin. Cleaving the peptide from the resin may be achieved using methods described above.

The peptide of formula 3 is taken up in DMF and stirred and ten equivalents of methyl iodide (MeI) are added dropwise to the mixture. After the MeI addition is complete, the reaction mixture is allowed to stir for an additional period of from fifteen minutes to one hour, preferably about thirty minutes, before it is concentrated to dryness to afford the isothiuronium iodide compound of formula 4.

At this point in the process, three alternative routes are possible which produce different end-products. If the reagent $R^3NH_2$ employed in step (b) of the process was a monoprotected diaminoalkane such as 1,2-diaminoethane or 1,3-diaminopropane, protected at one of the amino groups by a typical amino-protecting group such as BOC, in the product, 4 $R^3$ is a terminally-protected aminoalkyl group. If, on the other hand, in the reagent $R^3NH_2$ employed in step (b) the $R^3$ group was hydrogen, alkyl or alkoxyalkyl such as $-(CH_2)_mO(CH_2)_nCH_3$, in the product, 4, $R^3$ is hydrogen, alkyl or alkoxyalkyl.

In the former case, the protected amino-group of $R^3$ is next deprotected by conventional means and subsequently displaces the S-methyl group in step (d) of the process, resulting in either of the cyclized products 6 or 7. This step is carried out by allowing the deprotected peptide to react intramolecularly in the presence of a base such as triethylamine for a period of from about three to twelve hours, preferably overnight.

In the latter case where $R^3$ is hydrogen, an alkyl group, or an alkoxyalkyl group, $-(CH_2)_mO(CH_2)_nCH_3$, it is possible to attach a second group $R^4$ to the modified side chain by displacing the S-methyl group with ammonia, an alkylamine or alkoxyalkylamine, $R^4NH_2$. In this alternative, the peptide containing the amino acyl residue of formula 4 is treated with a solution of DMF containing ten equivalents of trifluoroacetic acid (TFA). This solution is then allowed to stir for thirty minutes before concentrating the solution to dryness. A 10% solution of ammonia, and alkylamine, or alkoxyalkylamine, $R^4NH_2$, in DMF is then added to the dried mixture and allowed to mix overnight. Again the mixture is concentrated to dryness and an equal amount of the 10% alkylamine or alkoxyalkylamine solution is added to the dried mixture. The mixture is stirred overnight and concentrated before purification using high pressure liquid chromatography (HPLC). Purification yields a purified peptide containing the amino acyl residue of formula 5.

If the peptide was not earlier cleaved from the resin, after the formation of the amino acyl residue of formula 3, a solution of methyl iodide (approximately 5%) in DMF is added to the resin and allowed to react overnight. The resin is washed, as above, with DCM/DMF and DCM, to afford the amino acyl residue of formula 4. A solution of a tertiary amine such as triethylamine (approximately 6%) in neat alkylamine is then added to the resin and the mixture is stirred for 48 hours. The triethylamine is then allowed to evaporate and the resin is washed, as above, with DCM/DMF and DCM. The resin is then dried in vacuo overnight over $P_2O_5$. The dried resin is then treated for, approximately, 1.25 hour with anhydrous HF in the presence of anisole at 0° C. to cleave the peptide from the resin. Purification of the completed peptide can then be accomplished by methods known to those skilled in the art.

The following examples are provided to serve as further illustration of the invention and not as a limitation of the invention. Except for where otherwise indicated, the following examples were carried out in the temperature range of about 15° C. to 30° C.

The following protocol may be used to synthesize the initial peptides found in the examples.

One g (0.6 mmol) of D-Ala-NH-resin (4-methyl-benzhydrylamine resin) was placed in the reaction vessel of a Milligen-Biosearch 9500 peptide synthesizer. Amino acids were then added sequentially according to the following synthetic cycle:

1. Deblocking, to remove the t-butoxycarbamate (t-BOC) group from the alpha-amino function of the peptide, is carried out using a solution of 45% trifluoroacetic acid (TFA), 2.5% anisole, 2.0% dimethyl phosphite, and 50.5% methylene chloride. The resin is prewashed with the deblocking solution for one minute and then the deblocking reaction is run for 20 minutes.

2. Base wash, used to remove and neutralize the TFA used for deblocking, is a solution of 10% N,N'-diisopropylethylamine in methylene chloride. After each deblocking step, the resin is washed three times (one minute per wash) with base wash solution.

3. The coupling reaction is carried out using a solution of a t-BOC protected amino acid derivative in a 3-fold molar excess of 0.3 M DMF along with a solution of diisopropylcarbodiimide (activator) in a 3-fold molar excess of 0.3 M methylene chloride solution. The activated amino acid is then coupled to the free alpha amino group of the peptide-resin. The reaction time is as described in the synthesis protocol.

4. After each coupling reaction step, the resin is washed with three one minute washes. The individual washes are: one with methylene chloride, one with (1:1) methylene chloride/DMF and one with DMF.

EXAMPLE 1

NAc-D2Nal-D4ClPhe-D3Pal-Ser-Tyr-DHarg($CH_2CH_3$)$_2$-Leu-Harg($CH_2CH_3$)$_2$Pro-DAlaNH$_2$(1)

Synthesis Protocol: The amino protected amino acids are coupled to the resin according the following order, number, and duration of couplings:

| # | Amino Acid Coupling | |
|---|---|---|
| 1. | BOC-Pro | two-1h |
| 2. | BOC-Lys(N-epsilon-FMOC) | two-1h |
| 3. | BOC-Leu | two-1h |

-continued

| # | Amino Acid Coupling | |
|---|---|---|
| 4. | BOC-D-Lys(N-epsilon-FMOC) | two-1h |
| 5. | BOC-Tyr(O-2-Br-CBZ) | two-1h |
| 6. | BOC-Ser(O-Bzl) | two-1h |
| 7. | BOC-D-3Pal | two-6h |
| 8. | BOC-D-4ClPhe | two-2h |
| 9. | BOC-D-2Nal | two-2h |
| 10. | Acetic acid | two-2h |

Upon completion of the synthesis the resin was treated with 30% piperidine in DMF solution for 4 hours to remove the 9-fluorenylmethyl carbamate (FMOC) protecting groups and give NAc-D2Nal-D4ClPhe-D3Pal-Ser-(O-Bzl)-Tyr(O-2-Br-CBZ)-DLys-Leu-Lys-Pro-DAlaNH-resin. The resin was then washed three times with (1:1) DCM/DMF and DCM. A solution of 1,1′-thiocarbonyldiimidazole (2.14 g in 20 mL DMF) was added to the resin and the mixture was bubbled for 1 hour. The resin was drained and washed three times with (1:1) DCM/DMF and DCM. A 10% solution of ethylamine/DMF (20 mL) was then added to the resin and the mixture was allowed to mix for 4 hours. The 10% ethylamine/DMF solution was drained from the resin, replaced with a fresh portion of 10% ethylamine/DMF (20 mL) and allowed to mix overnight. The resin was drained and washed three times with (1:1) DCM/DMF and three times with DCM. MeI (0.74 mL) in DMF (15 mL) was then added to the resin and allowed to react overnight. The resin was drained and washed three times with (1:1) DCM/DMF and three times with DCM. The resin was then treated with neat ethylamine (15 mL) containing triethylamine (1 mL) and stirred for 48 hours. The ethylamine was allowed to evaporate and the resin was washed three times with (1:1) DCM/DMF and three times with DCM. The resin was then dried in vacuo overnight over $P_2O_5$. The dry resin was then treated with anhydrous HF in the presence of anisole at 0° C. for 1.25 h to cleave the peptide from the resin. The excess reagent was removed in vacuo and the resin was washed with ether. The resin was then stirred at room temperature in a solution of (1:1:0.1) water/acetonitrile/acetic acid (50 mL) for 10 minutes, and filtered. The filtrate was lyophilized to give crude NAc-D2Nal-D4ClPhe-D3Pal-Ser-Tyr-DHarg(CH₂CH₃)₂-Leu-Harg(CH₂CH₃)₂-Pro-DAlaNH₂. The crude product was purified by HPLC using a (25×2.5 cm) Dynamax C-18 column (8 micron) with solvent mixtures varying in a gradient ranging from (89%:11%) to (32%:68%) water/acetonitrile, containing 0.1% TFA, over a period of 20 minutes. The UV detector was set at 254 nM and the pure product was eluted as a single peak at 27.65 min as the trifluoroacetate salt. FAB Mass spec. m/e 1569 (M+H)⁺. Amino Acid Anal: 1.0 Ala; 1.0 Pro; 1.0 Leu; 0.8 Tyr; 0.6 Ser; 0.9 3-Pal; 1.0 4-Cl-Phe.

EXAMPLE 2

NAc-D2Nal-D4ClPhe-D3Pal-Ser-Tyr-DHarg(CH₂CH₃)₂-Leu-Harg(CH₂CH₃)₂-Pro-DAlaNH₂

The procedure described in Example 1 was used through the FMOC cleavage to give NAc-D2Nal-D4ClPhe-D3Pal-Ser(O-Bzl)-Tyr(O-2-Br-CBZ)-DLys-Leu-Lys-Pro-DAlaNH-resin. The resin was then washed three times with (1:1) DCM/DMF and three times with DCM, and subsequently bubbled with a solution of 1,1′-thiocarbonyldiimidazole (2.14 g in 20 mL DMF) for 1 hour. The resin was then drained and washed three times with DCM/DMF (1/1) and three times with DCM. The resin was then mixed for 4 hours in a 10% solution of ethylamine/DMF (20 mL). The resin was drained and a fresh portion of 10% ethylamine/DMF (20 mL) was added to the resin and allowed to mix overnight. After the resin was drained and washed three times with (1:1) DCM/DMF and three times with DCM the resin was dried in vacuo overnight over $P_2O_5$. The dry resin was then treated with anhydrous HF in the presence of anisole at 0° C. for 1.25 h to cleave the peptide from the resin. The excess reagent was removed in vacuo and the resin was washed with ether. The resin was then stirred at room temperature in a solution of (1:1:0.1) water/acetonitrile/acetic acid (50 mL) for 10 minutes, and filtered. The filtrate was lyophilized to give crude NAc-D2Nal-D4ClPhe-D3Pal-Ser-Tyr-DLys(N-epsilon-ethylthiocarbonyl)-Leu-Lys(N-epsilon-ethylthiocarbonyl)-Pro-DAlaNH2 as a white powder. The peptide was taken up in DMF (20 mL) and stirred while MeI (0.74 mL) was added dropwise. The reaction was stirred for 30 minutes and then concentrated by rotary evaporation. A neat solution of ethylamine (15 mL) containing triethylamine (1 mL) was then added and the solution was stirred overnight. The reaction mixture was then concentrated to remove the ethylamine and another equal portion of neat ethylamine (15 mL) containing triethylamine (1 mL) was added and stirred for another 24 hours. After concentration, the residue was triturated in ether and taken up in a solution of (1:1:0.1) water/acetonitrile/acetic acid (50 mL) and lyophilized to give crude NAc-D2Nal-D4ClPhe-D3Pal-Ser-Tyr-DHarg(CH₂CH₃)₂-Leu-Harg(CH₂CH₃)₂-Pro-DAlaNH₂. The crude peptide was purified by HPLC using a (25×2.5 cm) Dynamax C-18 column (8 micron) with solvent mixtures varying in is a gradient ranging from (89%:11%) to (32%:68%) water/acetonitrile, containing 0.1% TFA,(89%:11%) to (32%:68%) water/acetonitrile, containing 0.1% TFA, over a period of 20 minutes. The UV detector was set at 254 nM and the pure product was eluted as a single peak at 27.65 rain as the trifluoroacetate salt. FAB Mass spec. m/e 1569(M+H)⁺. Amino Acid Anal: 1.0 Ala; 1.0 Pro; 1.0 Leu; 0.8 Tyr;0.6 Ser;0.9 3-Pal; 1.0 4-Cl-Phe.

EXAMPLE 3

3-(4-Fluorophenyl)propionyl-D1Nal-Ser-NMeTyr-DLys(Nic)-Leu-Harg(CH₂CH₃)₅-Pro-DAlaNH₂

The procedure and the protocol described in Example 1 was used except for the following substitutions: BOC-DLys(Nic) for BOC-DLys(FMOC), BOC-NMeTyr(O-2,6-Cl-Bzl) for BOC-Tyr(O-2-Br-CBZ), BOC-D1Nal for BOC-D3Pal, and 3-(4-Fluorophenyl)propionic acid for BOC-D4ClPhe. Upon completion of the synthetic protocol 3-(4-Fluorophenyl)propionyl-D1Nal-Ser(O-Bzl)-NMeTyr(O-2,6-Cl-Bzl)-DLys(Nic)-Leu-Lys(FMOC)-Pro-DAlaNH-resin was obtained. The resin was then treated with 30% piperidine/DMF (20 mL) to remove the FMOC protecting group. The Lys (closer to the C-terminus) was converted to the Harg(CH₂CH₃)₂ using a procedure analogous to that described in Example 1. The crude peptide was purified by HPLC to yield 3-(4-Fluorophenyl)propionyl-D1Nal-Ser-NMeTyr-DLys(Nic)-Leu-Harg(CH₂CH₃)₂-Pro-DAlaNH2 as the trifluoroacetate salt; $R_T$=30.60 min; FAB Mass spec. m/e 1370 (M+H)+. Amino Acid Anal: 1.0 Ala; 1.0 Pro; 1.0 Leu; 1.0 Lys; 0.9 NMeTyr;, 0.2 Ser.

EXAMPLE 4

NAc-D2Nal-D4ClPhe-D3Pal-Ser-NMeTyr-DLys(Nic)-Leu-Harg(CH$_2$CH$_3$)$_2$-Pro-DAlaNH$_2$ The procedure described in Example 1 was used with the following substitutions: BOC-DLys(Nic) for BOC-DLys(FMOC) and BOC-NMeTyr(O-2,6Cl-Bzl) for BOC-Tyr(O-2-Br-CBZ). Upon completion of the synthetic protocol NAc-D2Nal-D4ClPhe-D3Pal-Ser(O-Bzl)-NMeTyr(O-2,6-Cl-Bzl)-DLys(Nic)-Leu-Lys(FMOC)-Pro-DAlaNH-resin was obtained. The resin was then treated with 30% piperidine/DMF (20 mL) to remove the FMOC protecting group. The Lys$^8$ was converted to the Harg(CH$_2$CH$_3$)$_2$ using a procedure analogous to that described in Example 1. The crude peptide was then purified by HPLC to yield NAc-D2Nal-D4ClPhe-D3Pal-Ser-NMeTyr-DLys(Nic)-Leu-Harg(CH$_2$CH$_3$)$_2$-Pro-DAlaNH$_2$ as the trifluoroacetate salt; R$_T$=21.90 min; FAB Mass spec. m/e 1580 (M+H)+. Amino Acid Anal: 0.94 Ala; 0.97 Pro; 1.00 Lys; 1.09 Leu; 1.10 NMeTyr; 0.46 Ser.

EXAMPLE 5

NAc-D2Nal-D4ClPhe-D3Pal-Ser-Tyr-DHarg(CH$_2$CH$_2$OCH$_3$)$_2$-Leu-Harg(CH$_2$CH$_2$OCH$_3$)$_2$-Pro-DAlaNH$_2$ The peptide of example 5 was obtained using the same procedure and protocol described in Example 1 with the exception that ethylamine was replaced with methoxyethylamine. The crude product was purified by HPLC to give NAc-D2Nal-D4ClPhe-D3 Pal-Ser-Tyr-D Harg(CH$_2$CH$_2$OCH$_3$)$_2$-Leu-Harg(CH$_2$CH$_2$OCH$_3$)$_2$-Pro-DAlaNH$_2$ as the trifluoroacetate salt; R$_T$=19.80 min; FAB Mass spec. m/e 1690 (M+H)+; Amino Acid Anal: 1.02 Ala; 1.02 Pro; 1.05 Leu; 0.91 Tyr; 1.00 Pal; 0.87 4Cl-Phe.

EXAMPLE 6

NAc-D2Nal-D4ClPhe-D3Pal-Ser-NMeTyr-DCit-Leu-Harg(CH$_2$CH$_3$)$_2$-Pro-DAlaNH$_2$ The peptide of example 6 was obtained using the procedure described in Example 4 with the exception that BOC-DCit was substituted for BOC-DLys(FMOC). The crude product was purified by HPLC to give NAc-D2Nal-D4ClPhe-D3Pal-Ser-NMeTyr-DCit-Leu-Harg(CH$_2$CH$_3$)$_2$-Pro-DAlaNH$_2$ as the trifluoroacetate salt; R$_T$=25.80 min; FAB Mass spec. m/e 1514 (M+H)+. Amino Acid Anal: 1.00 Ala; 0.98 Pro; 1.02 Leu; 0.90 Cit; 0.75 NMeTyr; 0.45 Ser; 0.92 3Pal; 0.94 4ClPhe.

EXAMPLE 7

The procedure described in Example 6 was used through the FMOC cleavage to give NAc-D2Nal-D4ClPhe-D3Pal-Ser(O-Bzl)-NMeTyr(O-2,6-Cl-Bzl)-DCit-Leu-Lys-Pro-DAlaNH-resin. The resin was then bubbled in a solution of 1,1'-thiocarbonyldiimidazole (2.14 g in 20 mL DMF) for 1 hour, then washed three times with (1:1) DCM/DMF and three times with DCM. N-(t-butoxycarbonyl)ethylenediamine (0.95 g) was dissolved in DCM/DMF (1/1, 20 mL) then added to the resin. The resulting mixture was then bubbled for 2.5 hours. The resin was drained and washed three times with DCM/DMF (1/1) and three times with DCM. MeI (0.74 mL) in (1:1) DCM/DMF (20 mL) was then added to the resin. After 1 hour additional MeI solution (0.74 mL) was added, additional MeI solution (0.74 ml) was again added after another hour. After 3 hours of mixing, the solution was drained and the resin washed three times with (1:1) DCM/DMF and three times with DCM. The remaining BOC protecting group was removed by standard deblocking and base wash conditions (see Example 1 ). The resin was then treated with 10% diisopropylethylamine/DCM (20 mL) for 24 hours to cause ring cyclization. The solution was drained and the resin was washed three times with (1:1) DCM/DMF and three times with DCM. The resin was dried over P$_2$)$_5$ overnight and treated with anhydrous HF/anisole to cleave the protecting groups from the peptide and the peptide from the resin. The crude peptide was purified by HPLC to afford the title compound as the trifluoroacetate salt; R$_T$=22.4 min; FAB Mass spec. m/e 1484 (M+H)+. Amino Acid Anal: 1.03 Ala; 0.99 Pro; 0.98 Leu; 0.93 Cit; 0.76 NMeTyr; 0.37 Ser; 0.88 3Pal; 1.04 4ClPhe.

EXAMPLE 8

NAc-D2Nal-D4ClPhe-D3Pal-Ser-NMeTyr-DHarg(CH$_2$CH$_3$)$_2$-Leu-Harg(CH$_2$CH$_3$)$_2$-Pro-DAlaNH$_2$ The peptide of Example 8 was obtained using the same procedure and protocol described in Example 1 except that BOC-NMeTyr(O-2,6-Cl-Bzl) was substituted for BOC-Tyr(O-2-Br-CBZ). The crude peptide was purified by HPLC to give NAc-D2Nal-D4ClPhe-D3Pal-Ser-NMeTyr-DHarg(CH$_2$CH$_3$)$_2$-Leu-Harg(CH$_2$CH$_3$)$_2$-Pro-DAlaNH$_2$ as the trifluoroacetate salt.

EXAMPLE 9

NAc-D2Nal-D4ClPhe-D3Pal-Ser-NMeTyr-DCit-Leu-Harg(CH$_2$CH$_3$)-Pro-DAlaNH$_2$

The procedure described in Example 6 was used through the FMOC cleavage to give NAc-D2Nal-D4ClPhe-D3Pal-Ser(O-Bzl)-NMeTyr(O-2,6-Cl-Bzl)-DCit-Leu-Lys Pro-DAlaNH-resin. The resin was then bubbled for 1 hour in a solution of 1,1'-thiocarbonyldiimidazole (2.14 g in 20 mL DMF). The resin was drained and then washed three times with (1:1) DCM/DMF and three times with DCM. Subsequently,

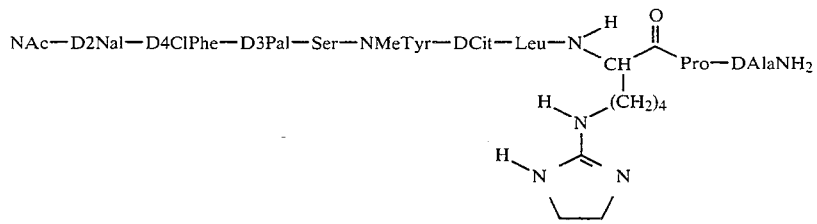

the resin was stirred with liquid ammonia (20 mL) at room temperature for 2 hours. The ammonia was evaporated and the resin washed three times with (1:1) DCM/DMF and three times with DCM. The resin was then bubbled in a solution of MeI (0.74 mL) in DCM/DMF (1/1, 20 mL). After 1 hour, trifluoroacetic acid (1.0 mL) was added and the resin bubbled for an additional 5 minutes. The solution was drained and the resin washed three times with (1:1) DCM/DMF and three times with DCM. The resin was then treated with neat ethylamine (20 mL) for 4 hours. The solution was evaporated and the resin washed three times with (1:1) DCM/DMF and three times with DCM. Drying over P$_2$O$_5$ in vacuo overnight, treatment with standard HF conditions, and purification by HPLC afforded pure NAc-D2Nal-D4ClPhe-D3Pal-Ser-NMeTyr-DCit-Leu-Harg(CH$_2$CH$_3$)-Pro-DAlaNH$_2$ as the trifluoroacetate salt. R $_T$=18.2 min; FAB Mass spec. m/e 1486 (M+H)$^+$. Amino Acid Anal: 1.02 Ala; 0.97 Pro; 1.02 Leu; 1.02 Cit; 0.92 NMeTyr; 0.49 Ser; 1.03 3Pal; 1.06 4ClPhe.

We claim:

1. A method of preparing peptides containing an aminoacyl residue of the structure

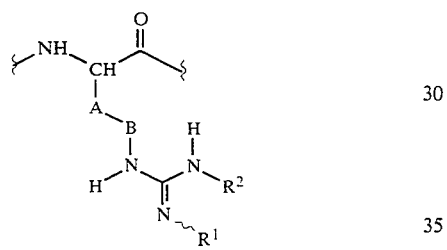

wherein A and B are selected from the group consisting of divalent straight or branched alkylene of from 1 to 8 carbon atoms and cis-, or trans-1,4-cyclohexylene, with the proviso that A and B may not both be cyclohexylene;

R$^1$ and R$^2$ are independently selected from the group consisting of hydrogen, straight or branched alkyl of from 1 to 6 carbon atoms, —(CH$_2$)$_m$O(CH$_2$)$_n$CH$_3$ wherein m is an integer of 2 to 4, inclusive, and n is an integer of 1 to 4, inclusive or R$^1$ and R$^2$ join, together with the nitrogen atoms to which they are attached, to form a 5- or 6 membered ring, provided that R$^1$ and R$^2$ are not both hydrogen;

the process of this invention comprising the steps of (a) first reacting the free amino group in the side chain of the aminoacyl residue of a functionally-protected resin-bound peptide containing an amino acyl residue of the structure

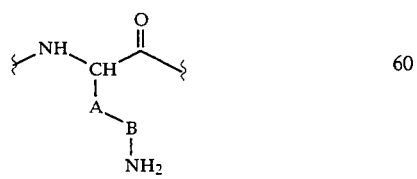

with 1,1′-thiocarbonyldiimidazole to form a protected peptide containing an aminoacyl residue of the structure

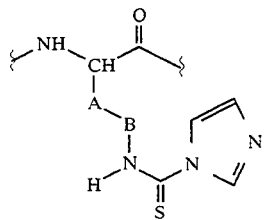

(b) reacting the product of step (a) with an amine, R$^3$NH$_2$, where R$^3$ is selected from the group consisting of
hydrogen,
protected 2-aminoethyl,
protected 3-aminopropyl,
straight or branched alkyl of 1 to 6 carbon atoms, and
—(CH$_2$)$_m$O(CH$_2$)$_n$CH$_3$,
to form a thiourea compound of the formula

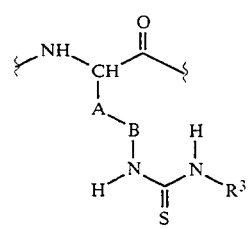

(c) reacting the product of step (b) with methyl iodide to form an isothiuronium iodide compound of the formula

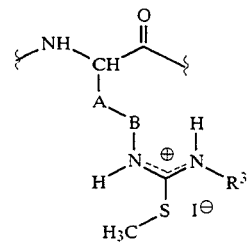

(d) when R$^3$ is an N-protected 2-aminoethyl or N-protected 3-aminopropyl, deprotecting the terminal amino group of R$^3$ to form a product of the formula

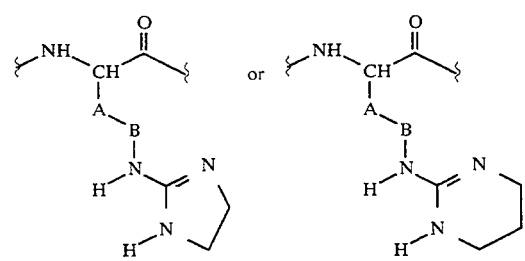

respectively, and
when R$^3$ is hydrogen, straight or branched alkyl of 1 to 6 carbon atoms or —(CH$_2$)$_m$O(CH$_2$)$_n$CH$_3$, reacting the isothiuronium iodide product of step (c) with an amine R$^4$NH2 where R$^4$ is selected from the group consisting of hydrogen, straight or branched alkyl of 1 to 6 carbon atoms and —(CH$_2$)$_m$O(CH$_2$)$_n$CH$_3$, where m and n are defined above, to form a product of the structure

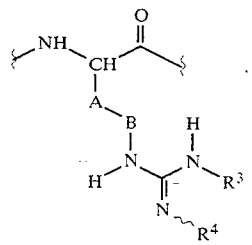

2. The process of claim 1 wherein the product is selected from peptides having an aminoacyl residue of the structure

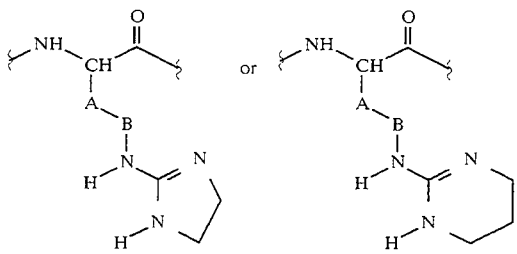

3. The process of claim 1 wherein $R^1$ and $R^2$ are independently selected from the group consisting of hydrogen, straight or branched alkyl of from 1 to 6 carbon atoms, —(CH$_2$)$_m$O(CH$_2$)$_n$CH$_3$ wherein m is an integer of 2 to 4, inclusive, and n is an integer of 1 to 4, inclusive, provided that $R_1$ and $R_2$ are not both hydrogen;

4. The process of claim 3 wherein one of $R^1$ and $R^2$ is hydrogen.

5. The process of claim 3 wherein A is butyl, B is absent and $R^1$ and $R^2$ are independently selected from alkyl of 1 to 6 carbon atoms and —(CH$_2$)$_m$O(CH$_2$)$_n$CH$_3$.

6. The process of claim 3 wherein $R^1$ and $R^2$ are ethyl.

* * * * *

UNITED STATES PATENT AND TRADEMARK OFFICE
CERTIFICATE OF CORRECTION

PATENT NO. : 5,432,263
DATED : July 11, 1995
INVENTOR(S) : FORTUNA HAVIV; ROLF E. SWENSON; TIMOTHY D. FITZPATRICK It is certified that error appears in the above-indentified patent and that said Letters Patent is hereby corrected as shown below:

| | |
|---|---|
| COLUMN 1, LINE 36: | Before the word "form" insert --to-- |
| COLUMN 1, LINE 44: | Replace "an" with --area-- |
| COLUMN 4, LINE 9: | Replace "an" with --area-- |
| COLUMN 6, LINE 21: | delete "which" |
| COLUMN 6, LINE 21: | delete "fast" |
| COLUMN 8, LINE 55: | delete "carded" insert --carried-- |
| COLUMN 10, LINE 5: | delete "1'-thiocarbonyl-diimidazole" insert --1,1'-thiocarbonyldiimidazole-- |
| COLUMN 14, LINE 51: | delete "Harg($CH_2CH_3$)$_5$" insert --Harg($CH_2CH_3$)$_2$-- |

UNITED STATES PATENT AND TRADEMARK OFFICE
CERTIFICATE OF CORRECTION

PATENT NO. : 5,432,263
DATED : July 11, 1995
INVENTOR(S) : FORTUNA HAVIV; ROLF E. SWENSON; TIMOTHY D. FITZPATRICK It is certified that error appears in the above-indentified patent and that said Letters Patent is hereby corrected as shown below:

COLUMN 15, LINE 38:     delete "Pal"
                                     insert --3Pal--

COLUMN 15, LINE 49:     delete "Harg($CH_2CH_3$)$_2$"
                                     insert --Harg($CH_2CH_3$)$_2$--

COLUMN 16, LINE 23:     delete "$P_2)_5$"
                                     insert --$P_2O_5$--

Signed and Sealed this

Twenty-first Day of November, 1995

Attest:

BRUCE LEHMAN

Attesting Officer      Commissioner of Patents and Trademarks